US012178205B2

(12) United States Patent
Benevenia et al.

(10) Patent No.: US 12,178,205 B2
(45) Date of Patent: Dec. 31, 2024

(54) SYSTEMS AND METHODS FOR STORING AND PRESERVING IMPLANTABLE DEVICES

(71) Applicant: Rutgers, The State University of New Jersey, New Brunswick, NJ (US)

(72) Inventors: Joseph Benevenia, Montclair, NJ (US); Sheldon S. Lin, Chatham, NJ (US); Michael J. Vives, Newark, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 851 days.

(21) Appl. No.: 17/307,493

(22) Filed: May 4, 2021

(65) Prior Publication Data

US 2021/0251215 A1    Aug. 19, 2021

Related U.S. Application Data

(63) Continuation-in-part of application No. 15/425,617, filed on Feb. 6, 2017, now Pat. No. 11,224,678.

(Continued)

(51) Int. Cl.
*A61F 2/00* (2006.01)
*A01N 1/02* (2006.01)
(Continued)

(52) U.S. Cl.
CPC ......... *A01N 1/0242* (2013.01); *A01N 1/0205* (2013.01); *A01N 1/0263* (2013.01);
(Continued)

(58) Field of Classification Search
CPC .... A01N 1/0205; A01N 1/0263; A01N 59/16; A61F 2/0095
See application file for complete search history.

(56) References Cited

U.S. PATENT DOCUMENTS

| | | | | |
|---|---|---|---|---|
| 4,759,445 A | * | 7/1988 | McVay | C08J 3/223 206/524.5 |
| 4,813,210 A | * | 3/1989 | Masuda | A61L 2/26 53/472 |

(Continued)

FOREIGN PATENT DOCUMENTS

| | | |
|---|---|---|
| JP | 2001-523527 A | 11/2001 |
| JP | 2015113299 A | 6/2015 |
| WO | 08032928 A1 | 3/2008 |

OTHER PUBLICATIONS

Qayyum et al: "The Antimicrobial Activity of Different Zinc Salts", Proceedings S.Z.P.G.M.I. vol: 12(1-2), 1998, pp. 8-12.

(Continued)

*Primary Examiner* — Jacob K Ackun
(74) *Attorney, Agent, or Firm* — FOX ROTHSCHILD LLP

(57) ABSTRACT

This disclosure provides systems and methods for storing and preserving an implantable device. The system comprises a first sealable container; a second sealable container housed within the first sealable container; and a storage solution comprising a zinc compound contained in the second sealable container. The storage solution exhibits antimicrobial activity of inhibiting or controlling growth of microbial organisms and is capable of maintaining the implantable device in a hydrated state.

19 Claims, 1 Drawing Sheet

Related U.S. Application Data

(60) Provisional application No. 63/019,525, filed on May 4, 2020, provisional application No. 62/293,064, filed on Feb. 9, 2016.

(51) Int. Cl.
    *A01N 59/16* (2006.01)
    *A61F 2/08* (2006.01)

(52) U.S. Cl.
    CPC ............ *A01N 59/16* (2013.01); *A61F 2/0095* (2013.01); *A61F 2/08* (2013.01)

(56) References Cited

U.S. PATENT DOCUMENTS

| | | | |
|---|---|---|---|
| 5,454,886 A | 10/1995 | Burrell et al. | |
| 5,520,664 A * | 5/1996 | Bricault, Jr. | A61L 29/16 604/174 |
| 5,906,825 A * | 5/1999 | Seabrook, Jr. | A01N 25/10 424/404 |
| 6,013,106 A | 1/2000 | Tweden et al. | |
| 6,113,636 A | 9/2000 | Ogle | |
| 6,254,294 B1 * | 7/2001 | Muhar | A61F 17/00 401/26 |
| 6,337,052 B1 | 1/2002 | Rosenwasser | |
| 9,238,090 B1 | 1/2016 | Fette | |
| 2007/0185026 A1 * | 8/2007 | Walsh | A61L 15/46 424/234.1 |
| 2007/0207186 A1 * | 9/2007 | Scanlon | A61F 2/91 623/1.42 |
| 2011/0140316 A1 | 6/2011 | Bagga et al. | |
| 2013/0028981 A1 | 1/2013 | Gratzer | |
| 2013/0277242 A1 * | 10/2013 | Mori | A61L 12/086 206/205 |
| 2013/0280223 A1 | 10/2013 | Owens et al. | |
| 2014/0021208 A1 | 1/2014 | Anti et al. | |
| 2014/0147487 A1 | 5/2014 | Walls | |
| 2014/0271779 A1 | 9/2014 | Bagga et al. | |
| 2015/0004249 A1 | 1/2015 | Lin et al. | |
| 2015/0239640 A1 | 8/2015 | Smith et al. | |
| 2015/0351893 A1 | 12/2015 | Smith et al. | |
| 2017/0106119 A1 | 4/2017 | Skinner et al. | |
| 2017/0224871 A1 | 8/2017 | Benevenia et al. | |
| 2019/0274809 A1 | 9/2019 | Kapec et al. | |
| 2019/0358366 A1 * | 11/2019 | Zawko | A61L 27/3633 |
| 2021/0251215 A1 | 8/2021 | Benevenia et al. | |

OTHER PUBLICATIONS

Delloye, et al: "Bone Allografts: What They Can Offer and What They Cannot", 2007, The Bone & Joint Journal, vol. 39, No. 5, pp. 574-579.

Maral, et al: "Effectiveness of Human Amnion Preserved Long-Term in Glycerol as a Temporary Biological Dressing", Burns, 1999, 25, pp. 625-635.

Faiz, et al: "Efficacy of Zinc as Antibacterial Agent Against Enteric Bacterial Pathogens", J. Ayub Med Coll Abbottabad, 2011, vol. 23, No. 2, pp. 20.

Aho, et al: "Clinical Use of Bone Allografts", Annals of Medicine, 1993, 25:4, pp. 403-412, DOI: 10.3109/07853899309147303.

Lord, et al: "Infection in Bone Allografts", Incidence, Nature, and Treatment, The Journal of Bone and Joint Surgery,. Mar. 1988, vol. 70, pp. 369-376.

Muscolo, et al: "The Use of a Bone Allograft for Reconstruction after Resection of Giant-Cell Tumor Close to the Knee", The Journal of Bone and Joint Surgery, Nov. 1993, vol. 75, No. 11, pp. 1656-1662.

Tomford, et al: "Frozen Musculoskeletal Allografts, A Study of the Clinical Incidence and Causes of Infection Associated with Their Use", The Journal of Bone and Joint Surgery, Sep. 1990, vol. 72, No. 8, pp. 1137-1143.

Mankin, et al: "Infection in Massive Bone Allografts", Clinical Orthopaedics and Related Research, 2005, No. 432, pp. 210-216.

* cited by examiner

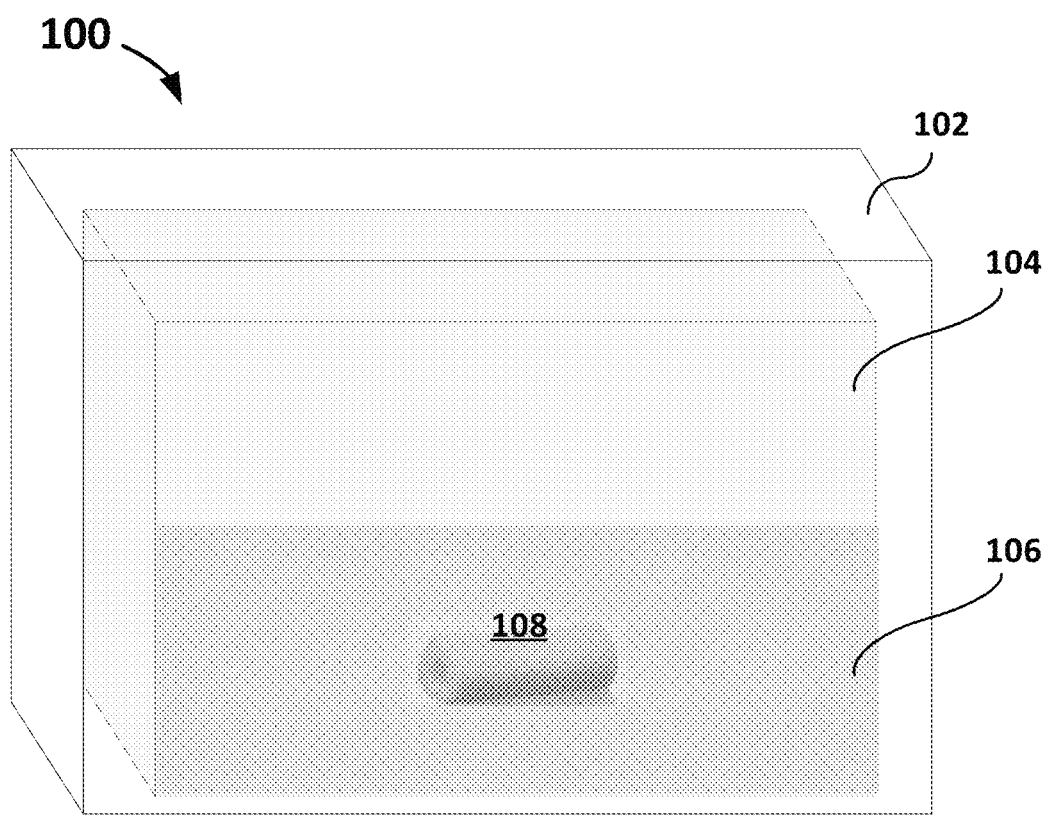

SYSTEMS AND METHODS FOR STORING AND PRESERVING IMPLANTABLE DEVICES

CROSS-REFERENCE TO RELATED APPLICATIONS

The present application is a continuation-in-part of U.S. Nonprovisional patent application Ser. No. 15/425,617, filed Feb. 6, 2017, which issued as U.S. Pat. No. 11,224,678 on Jan. 18, 2022, which claims the benefit of priority under 35 U.S.C. § 119 (e) to U.S. Provisional Patent Application No. 62/293,064, filed Feb. 9, 2016. This application also claims priority under 35 U.S.C. § 119 (e) to U.S. Provisional Patent Application No. 63/019,525, filed May 4, 2020. The foregoing applications are incorporated by reference herein.

FIELD

This disclosure relates to systems and methods of storing and preserving implantable devices and more specifically to systems and methods of storing and preserving implantable devices, such as tissue grafts, for subsequent surgical procedures.

BACKGROUND

The traditional method of preserving musculoskeletal grafts, such as allografts, is by the process of freeze-drying (i.e., lyophilizing) the graft. This process involves slow freezing the processed tissue while slowly drawing a vacuum on a chamber in which the tissue grafts have been placed. This process removes the water content by sublimation without forming large ice crystals that may damage the tissue. By driving the residual moisture in the grafts to 6% or lower, microbial (e.g., bacterial and fungal) growth can be halted, and enzymatic degradation can be slowed by several orders of magnitude. However, freeze-dried (i.e., lyophilized) grafts require hydration before implantation, which can take up to long periods of time. For large grafts, i.e., massive proximal femoral allografts used for hip reconstruction after resection of a bony tumor, four hours or more can be required to properly hydrate before implantation into the subject. For smaller grafts, such as those used for spinal surgery, 10 to 60 minutes or more can be required to re-hydrate the graft. For this reason, lyophilized grafts are often not hydrated properly prior to implantation due to time constraints and other factors. Therefore, these lyophilized graft canals often have diminished strength (i.e., the force required to break the bone) and diminished toughness (less resistance to fracture, i.e., more brittle), making them prone to cracking if not adequately hydrated.

Furthermore, once cracks form in a bone graft, they typically continue to grow unless solid bony fusion occurs first. Sometimes such cracking leads to complications in the subject, i.e., unstable constructs in the spine or other bony regions. A cracked graft may necessitate revision surgery. In some instances, a cracked graft can collapse and/or shift in the surgical site and may result in neurological and/or vascular injury to the subject.

This scenario can present various problems. For example, grafts can crack while the surgeon is inserting the implant to the surgical site, which sometimes requires tapping with a mallet, in which the graft canal can crack after implantation. Accordingly, it is desirable to ensure that grafts are fully hydrated prior to being implanted to maximize the material toughness and to minimize the potential for cracking. Additionally, precision cut and computer numerical control (CNC)-machined bone grafts can shrink upon lyophilization and then expand upon hydration. The shrink factors are anisotropic; that is, they are a function of direction of the axis of the bone from which they were cut. For example, with long bones (e.g., cortical bone), the shrink factors in the circumferential and radial directions of the long bone are typically similar, and the shrink factor in the longitudinal direction can be substantially different. For precision cut and CNC-machined grafts, the change in dimensions can cause problems with the grafts properly interfacing with the surgical instruments and fitting into the prepared surgical site.

To maintain full biomechanical strength and toughness of grafts, some have utilized an alternative preservation method of freezing cortical bone grafts, ligaments, tendons, and other tissue, such as costal cartilage, at 40° C. or less, and then thawing the grafts in normal saline at the time of surgery. Thawing takes about 1 to 5 minutes with small grafts, such as those used for structural interbody support in the spine, or about 10 to 60 minutes for larger grafts. However, this preservation method requires that a validated and continuously monitored −80° C. freezer be present at any location where these grafts are to be stored. Alternatively, the grafts can be shipped on dry ice to the location where the grafts are to be used and can then be returned to the tissue bank or other storage facility on dry ice if the grafts are not implanted. Thus, this method is relatively complex and expensive and is not feasible in allocations. Freezing also creates crystals that would weaken the structural integrity of graft crystals form.

Surgeons are frequently faced with reconstruction challenges caused by bone loss. Although autologous bone is the gold standard for bone restoration, donor site morbidity and limited bone volume have led to increased utilization of allograft bone. Approximately 800,000 bone allograft transplantations are performed yearly in the United States, making bone the second most commonly transplanted tissue as described in Boyce et al. (Boyce et al. Orthop Clin North Am. 1999 October; 30 (4): 571-81). Although bone allograft generally restores bone mass, complications such as graft-host nonunion, fracture, and graft infection are not infrequent as described in Aho A J. Ann Med. 1993; 25:403-412.

Allograft-associated infection often requires removal of infected bone and extensive debridement of the affected site with substantial patient morbidity as described by Muscolo D L et al. The use of a bone allograft for reconstruction after resection of giant-cell tumor close to the knee. J Bone Joint Surg. Am. 1993; 75:1656-1662. Most of these allograft-associated infections can occur early, such as within four months (Lord et al., J. Bone Joint Surg. Am. 1988; 70:369-376; Tomford W W et al. J. Bone Joint Surg. Am. 1990; 72:1137-1143) and despite extended antibiotic prophylaxis (Mankin H J et al. Clin Orthop Relat Res. 2005; 432:210-216), the reported incidence remains at 4% to 12% (Lord C F et al.). Like metallic implants, allografts act as highly porous, non-cellular, and avascular foreign bodies that are prone to bacterial adhesion.

Hence, there remains a need for simple and cost-effective systems and methods for storing and preserving implantable devices such as tissue grafts at an ambient temperature range. There also remains a need for systems and methods for storing and preserving implantable devices, such as tissue grafts, so that the strength, shape, and dimensions of the grafts are maintained.

BRIEF DESCRIPTION OF THE DRAWINGS

The sole drawing FIGURE shows an example system for storing and preserving implantable devices.

SUMMARY

In one aspect, this disclosure provides a system for storing and preserving a hydrated implantable device. The system comprises: (i) a first sealable container; (ii) a second sealable container housed within the first sealable container; and (iii) a storage solution comprising a zinc compound contained in the second sealable container, wherein the storage solution exhibits antimicrobial activity of inhibiting or controlling growth of microbial organisms and is capable of maintaining the implantable device in a hydrated state.

In some embodiments, the first sealable container or the second sealable container is a bag, a box, a jar, or a tube. In some embodiments, the second sealable container is sterilized. In some embodiments, the second sealable container is removably housed within the first sealable container.

In some embodiments, the system further has an insulation layer disposed between the first sealable container and the second sealable container, wherein the insulation layer separates a least a portion of the first sealable container from the second sealable container. In some embodiments, the insulation layer is configured to reduce heat transmission between the first sealable container and the second sealable container.

In some embodiments, the first sealable container or the second sealable container is formed of steel, aluminum, glass, plastic, paper composite, or ceramic material. In some embodiments, the plastic material comprises a polymer selected from the group consisting of polyolefins, polyesters, polyamide, polyvinylchloride, acrylic, polycarbonates, polyethylene naphthalate (PEN), polyethylene terephthalate (PET), polystyrene, polyurethane, and mixtures thereof.

In some embodiments, the zinc compound is an inorganic zinc compound. In some embodiments, the inorganic zinc compound is selected from zinc chloride, zinc sulfate, zinc phosphate, zinc carbonate, and zinc nitrate, zinc chlorate, zinc chromate, and combinations thereof.

In some embodiments, the zinc compound is an organic zinc salt. In some embodiments, the organic zinc salt is selected from zinc acetate, zinc formate, zinc propionate, zinc gluconate, bis(maltolato)zinc, zinc acexamate, zinc aspartate, bis(maltolato)zinc(II) [$Zn(ma)_2$], bis(2-hydroxypyridine-N-oxido)zinc(II) [$Zn(hpo)_2$], bis(allixinato) Zn(II) [$Zn(alx)_2$], bis(6-methylpicoli-nato) Zn(II) [$Zn(6mpa)_2$], bis(aspirinato)zinc(II), bis(pyrrole-2-carboxylato)zinc [$Zn(pc)_2$], bis(alpha-furonic acidato)zinc [$Zn(fa)_2$], bis(thiophene-2-carboxylato)zinc [$Zn(tc)_2$], bis(thio-phene-2-acetato)zinc [$Zn(ta)_2$], (N-acetyl-L-cysteinato) Zn(II) [Zn(nac)], zinc(II)/poly(γ-glutamic acid) [$Zn(\gamma\text{-}pga)$], bis(pyrrolidine-N-dithiocarbamate)zinc(II) [$Zn(pdc)_2$], zinc(II) L-lactate [$Zn(lac)_2$], zinc(II) D-(2)-quinic acid [$Zn(qui)_2$], bis(1,6-dimethyl-3-hydroxy-5-methoxy-2-pentyl-1,4-dihydropyridine-4-thionato)zinc(II) [$Zn(tanm)_2$], β-alanyl-L-histidinato zinc(II) (AHZ), or the like, or combinations thereof.

In some embodiments, the storage solution contains between about 1 mM and about 1 M zinc chloride. In some embodiments, the storage solution comprises between about 0.1 wt % and about 20 wt % zinc chloride.

In some embodiments, the implantable device is a tissue article. In some embodiments, the implantable device is a tissue graft. In some embodiments, the tissue graft is selected from allograft bone, autograft bone, xenograft bone, allograft cartilage, amniotic tissue, ligament tissue, tendon tissue, porous tissue, and soft tissue. In some embodiments, the implantable device can be an allograft tissue. In some embodiments, the soft tissue is a ligament or a tendon.

In another aspect, this disclosure provides a method for storing and preserving a hydrated implantable device in an implant storage device, wherein the implant storage device comprises: a first sealable container; a second sealable container housed within the first sealable container; and a storage solution containing a zinc compound contained in the second sealable container, wherein the storage solution exhibits antimicrobial activity of inhibiting or controlling growth of microbial organisms and is capable of maintaining the implantable device in a hydrated state. The method may include: placing the implantable device in the second sealable container, thereby causing at least a portion of the implantable device to be in direct contact with the storage solution; and keeping the implantable device in the storage solution for a predetermined period of time.

In some embodiments, the method further includes rinsing the implantable device with the storage solution prior to placing the implantable device in the second sealable container. In some embodiments, the step of keeping includes keeping the implantable device in the storage solution from about minutes to about two years (e.g., 1 month, 2 months, 4 months, 6 months, 8 months, 10 months, 12 months, 14 months, 16 months, 18 months, 20 months, 22 months, 24 months). In some embodiments, the step of keeping further includes keeping the implantable device in the storage solution at about 25° C.

In some embodiments, the first sealable container or the second sealable container is a bag, a box, a jar, or a tube. In some embodiments, the second sealable container is sterilized. In some embodiments, the second sealable container is removably housed within the first sealable container. In some embodiments, the implant storage device further comprises an insulation layer disposed between the first sealable container and the second sealable container, wherein the insulation layer separates a least a portion of the first sealable container from the second sealable container. In some embodiments, the insulation layer is configured to reduce heat transmission between the first sealable container and the second sealable container.

In some embodiments, the first sealable container or the second sealable container is formed of steel, aluminum, glass, plastic, paper composite, or ceramic material. In some embodiments, the plastic material comprises a polymer selected from polyolefins, polyesters, polyamide, polyvinylchloride, acrylic, polycarbonates, polyethylene naphthalate (PEN), polyethylene terephthalate (PET), polystyrene, polyurethane, and mixtures thereof.

In some embodiments, the zinc compound is an inorganic zinc compound. In some embodiments, the inorganic zinc compound is selected from zinc chloride, zinc sulfate, zinc phosphate, zinc carbonate, and zinc nitrate, zinc chlorate, zinc chromate, and combinations thereof. In some embodiments, the zinc compound comprises an organic zinc salt. In some embodiments, the organic zinc salt is selected from the group consisting of zinc acetate, zinc formate, zinc propionate, zinc gluconate, bis(maltolato)zinc, zinc acexamate, zinc aspartate, bis(malto-lato)zinc(II) [$Zn(ma)_2$], bis(2-hydroxypyridine-N-oxido)zinc(II) [$Zn(hpo)_2$], bis(allixinato) Zn(II) [$Zn(alx)_2$], bis(6-methylpicolinato) Zn(II) [$Zn(6mpa)_2$], bis(aspirinato)zinc(II), bis(pyrrole-2-carboxylato)zinc [$Zn(pc)_2$], bis(alpha-furonic acidato)zinc [$Zn(fa)_2$], bis(thiophene-2-carboxyl-ato)zinc [$Zn(tc)_2$], bis(thiophene- 2-acetato)zinc [Zn(ta)$_2$], (N-acetyl-L-cysteinato) Zn(II) [Zn(nac)], zinc(II)/poly(γ-glutamic acid) [Zn(γ-pga)], bis(pyrrolidine-N-dithiocarbamate)zinc(II) [Zn(pdc)$_2$], zinc(II) L-lactate [Zn(lac)$_2$], zinc(II) D-(2)-quinic acid [Zn(qui)$_2$], bis(1,6-dimethyl-3-hydroxy-5-methoxy-2-pentyl-1,4-dihydropyridine-4-thionato)zinc(II) [Zn(tanm)$_2$], β-alanyl-L-histidinato zinc(II) (AHZ), or the like, or combinations thereof. In some embodiments, the storage solution contains between about 1 mM and about 1 M zinc chloride. In some embodiments, the storage solution comprises between about 0.1 wt % and about 20 wt % zinc chloride. In some embodiments, the storage solution further includes sodium bicarbonate.

In yet another aspect, this disclosure further provides a kit for storing a hydrated implantable device, including: (i) a first sealable container; (ii) a second sealable container housed within the first sealable container; and (iii) a third container containing a storage solution containing a zinc compound, wherein the storage solution exhibits antimicrobial activity of inhibiting or controlling growth of microbial organisms and is capable of maintaining the implantable device in a hydrated state.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the disclosure will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DETAILED DESCRIPTION

This disclosure provides systems and methods of storing and preserving hydrated implantable devices. The system includes a storage solution containing zinc ions provided by appropriate zinc compounds for prevention of infection in which an implantable device (e.g., surgical implant) is stored. The zinc ions possess antimicrobial activities and are capable of modifying the surface of implantable devices, thereby providing deep cleaning and effective protection against microbial infection. The system offers a long shelf life (e.g., one month, three months, six months, one year or more) for implantable devices.

When the implantable device has surface calcium ion, one novel concept lies in a competitive binding concept involving ion exchange or substitution between zinc ions and calcium ions. Calcium ions are present, for example, in hydroxyapatite, a major component and an essential ingredient of normal bone and teeth. Hydroxyapatite, also called hydroxylapatite (HA), is a naturally occurring mineral form of calcium apatite with the formula Ca$_5$(PO$_4$)$_3$(OH), but it is usually written Ca$_{10}$(PO$_4$)$_6$(OH)$_2$ to denote that the crystal unit cell comprises two entities. Hydroxyapatite is the hydroxyl endmember of the complex apatite group. The OH ion can be replaced by fluoride, chloride or carbonate, producing fluorapatite or chlorapatite. It crystallizes in the hexagonal crystal system. Octacalcium phosphate (OCP), which is structurally similar to hydroxyapatite (HA), is a possible precursor of bone apatite crystals. Although disagreement remains as to whether OCP comprises the initial mineral crystals in the early stage of bone mineralization, the results of recent biomaterial studies using synthetic OCP indicate the potential role of OCP as a bone substitute material, owing to its highly osteoconductive and biodegradable characteristics. OCP tends to convert to HA not only in an in vitro environment, but also as an implant in bone defects.

It was found that when the foreign ions, e.g., zinc ions, substitute for Ca sites on HA or OCP, the surrounding oxygen ions undergo considerable inward relaxation, due to their smaller ionic sizes than Ca2+, which results in the smaller coordination numbers with oxygen as compared with those of Ca in bulk HA and OCP. Nevertheless, ion exchange or substitution of calcium ions with zinc ions modifies the surface of HA- or OCP-containing implantable devices, such as bone grafts. It also allows zinc ions to be absorbed into a deeper layer of implantable devices. As a result, zinc ions can be retained in implantable devices for a prolonged period of time.

Systems and Methods for Storing and Preserving Implantable Devices

In one aspect, this disclosure provides systems for packaging and storing hydrated implantable devices, such as tissue, for future use in a surgical procedure. As disclosed herein, embodiments of the present disclosure allow for tissue such as allograft to be effectively placed in a container and remain hydrated during storage. The disclosed system allows for the tissue to simply be removed from the container and used in the surgical procedure.

The system may include a storage solution for storing an implantable device, such as a tissue graft. In some embodiments, the storage solution includes water and an additional substance, including zinc salt, sodium bicarbonate or a combination thereof.

The implantable device may include a tissue graft for use as a surgical implant. In one embodiment, a bone allograft is provided, which can be sealed in a container with a volume of a solution and maintained in a hydrated state until its application in a surgical procedure. The amount of the solution is sufficient to submerge at least a portion of the implantable device. In some embodiments, the container housing the implantable device is disposed within an outer container.

With reference to the figure, system 100 for storing and preserving hydrated implantable devices is provided. The system 100 includes (i) a first sealable container 102; (ii) a second sealable container 104 housed within the first sealable container 102; and (iii) a storage solution 106 containing a zinc compound contained in the second sealable container 104, wherein the storage solution exhibits antimicrobial activity of inhibiting or controlling growth of microbial organisms and is capable of maintaining the implantable device 108 in a hydrated state.

The term "antimicrobial activity" means in the context of the present disclosure that the antimicrobial of the disclosure is active in inhibiting or controlling growth of microbial organisms, including fungal organisms and/or bacterial organisms, such as gram-positive and gram-negative bacteria. The antimicrobial activity can occur after the implantable device is implanted into the body.

In some embodiments, the antibacterial activity is the activity for bacterium selected from the group consisting of Pseudomonas aeruginosa, Staphylococcus aureus, Aspergillus brasiliensis spores, and Escherichia coli.

The containers as disclosed herein (e.g., first sealable container, second sealable container) can be liquid-tight containers. The containers can be made to have a wide variety of structural configurations and can be made from many different materials. The containers provide an impermeable barrier for the protection of the storage solution or implantable devices from materials that might come in contact with the exterior of the containers. Adequate protection of the stored substance, e.g., storage solution, implantable device, includes the ability of the containers to protect substances from ingress of liquids or gases, light, microorganisms, vermin, physical shock, crushing forces, vibration, leaking, or spilling. The containers must not impart or leach foreign materials into the contained substance. The containers must also be chemically resistant or inert in relation to the contained substance. Most containers utilize a coating or liner to ensure that the substances receive adequate protection, with the exception of glass containers. For glass containers, thick walls may be provided the requisite toughness to prevent shattering.

The first sealable container or the second sealable container can have various shapes or dimensions. In some embodiments, the first sealable container or the second sealable container is a bag, a box, a jar, or a tube. In some embodiments, the second sealable container is sterilized. In some embodiments, the second sealable container is removably housed within the first sealable container. For example, if needed, the second sealable container can be removed from the first sealable container during the surgical procedure. In some embodiments, the second sealable container can be mounted or attached to the first sealable container. In some embodiments, the first sealable container and the second sealable container can be formed in one piece.

In some embodiments, the second sealable container is substantially fitted within the first sealable container. In some embodiments, the system further comprises an insulation layer disposed between the first sealable container and the second sealable container, wherein the insulation layer separates a least a portion of the first sealable container from the second sealable container. In some embodiments, the insulation layer is configured to reduce heat transmission between the first sealable container and the second sealable container. In some embodiments, the insulation layer may be a vacuum.

The first sealable container or the second sealable container can be formed of any suitable materials. In addition, the first sealable container or the second sealable container can be formed of the same or different materials. In some embodiments, the first sealable container or the second sealable container can be formed of steel, aluminum, glass, plastic, paper composite, or ceramic material. In some embodiments, the plastic material comprises a polymer selected from the group consisting of polyolefins, polyesters, polyamide, polyvinylchloride, acrylic, polycarbonates, polyethylene naphthalate (PEN), polyethylene terephthalate (PET), polystyrene, polyurethane, and mixtures thereof.

In some embodiments, the zinc compound is an inorganic zinc compound. In some embodiments, the inorganic zinc compound is selected from zinc chloride, zinc sulfate, zinc phosphate, zinc carbonate, and zinc nitrate, zinc chlorate, zinc chromate, and combinations thereof.

In some embodiments, the zinc compound is an organic zinc salt. In some embodiments, the organic zinc salt is selected from zinc acetate, zinc formate, zinc propionate, zinc gluconate, bis(maltolato)zinc, zinc acexamate, zinc aspartate, bis(maltolato)zinc(II) [$Zn(ma)_2$], bis(2-hydroxypyridine-N-oxido)zinc(II) [$Zn(hpo)_2$], bis(allixinato) Zn(II) [$Zn(alx)_2$], bis(6-methylpicolinato) Zn(II) [$Zn(6mpa)_2$], bis(aspirinato)zinc(II), bis(pyrrole-2-carboxylato)zinc [$Zn(pc)_2$], bis(alpha-furonic acidato)zinc [$Zn(fa)_2$], bis(thiophene-2-carboxylato)zinc [$Zn(tc)_2$], bis(thio-phene-2-acetato)zinc [$Zn(ta)_2$], (N-acetyl-L-cysteinato) Zn(II) [Zn(nac)], zinc(II)/poly(γ-glutamic acid) [Zn(γ-pga)], bis(pyrrolidine-N-dithiocarbamate)zinc(II) [$Zn(pdc)_2$], zinc(II) L-lactate [$Zn(lac)_2$], zinc(II) D-(2)-quinic acid [$Zn(qui)_2$], bis(1,6-dimethyl-3-hydroxy-5-methoxy-2-pentyl-1,4-dihydropyridine-4-thionato)zinc(II) [$Zn(tanm)_2$], β-alanyl-L-histidinato zinc(II) (AHZ), or the like, or combinations thereof.

In some embodiments, the storage solution comprises between about 1 mM and about 1 M zinc chloride. In some embodiments, the storage solution comprises between about 0.1 wt % and about 20 wt % zinc chloride.

In some embodiments, the implantable device is tissue. In some embodiments, the implantable device is a tissue graft. In some embodiments, the tissue graft is selected from allograft bone, autograft bone, xenograft bone, allograft cartilage, amniotic tissue, ligament tissue, tendon tissue, porous tissue, and soft tissue. In some embodiments, the implantable device can be an allograft tissue. In some embodiments, the soft tissue is a ligament or a tendon. In some embodiments, a suitable allograft cartilage is manufactured by Anthrex as BIOCARTILAGE. In some embodiments the implantable device is a bone repair composition or cement containing hydroxyapatite (HA) or octacalcium phosphate (OCP).

In another aspect, this disclosure provides a method for storing and preserving a hydrated implantable device in an implant storage device, wherein the implant storage device includes: a first sealable container; a second sealable container housed within the first sealable container; and a storage solution containing a zinc compound contained in the second sealable container, wherein the storage solution exhibits antimicrobial activity of inhibiting or controlling growth of organisms and is capable of maintaining the implantable device in a hydrated state. The method may include: (a) placing the implantable device in the second sealable container, thereby causing at least a portion of the implantable device to be in direct contact with the storage solution; and (b) keeping the implantable device in the storage solution for a predetermined period of time.

In some embodiments, the method further includes rinsing the implantable device with the storage solution prior to placing the implantable device in the second sealable container.

The antimicrobial activity of zinc ions depends on its concentration and contact duration. In some embodiments, the storage solution contains between about 1 mM and about 1 M zinc chloride (e.g., 1 mM to 20 mM, 1 mM to 40 mM, 1 mM to 60 mM, 1 mM to 80 mM, 1 mM to 100 mM, 1 mM to 200 mM, 1 mM to 250 mM, 1 mM to 300 mM, 1 mM to 400 mM, 1 mM to 500 mM, 1 mM to 600 mM, 1 mM to 700 mM, 1 mM to 800 mM, 1 mM to 900 mM). In some embodiments, the storage solution contains between about 0.1 wt % and about 20 wt % zinc chloride (e.g., from 0.1 wt % to 0.5 wt %, from 0.1 wt % to 1 wt %, from 1 wt % to 2 wt %, from 1 wt % to 4 wt %, from 1 wt % to 6 wt %, from 1 wt % to 8 wt %, from 1 wt % to 10 wt %, from 1 wt % to 12 wt %, from 1 wt % to 14 wt %, from 1 wt % to 16 wt %, from 1 wt % to 18 wt %, from 1 wt % to 20 wt %).

In some embodiments, the step of keeping further includes keeping the implantable device in the storage solution for about 10 minutes to about 2 years (e.g., 1 month, 2 months, 4 months, 6 months, 8 months, 10 months, 12 months, 14 months, 16 months, 18 months, 20 months, 22 months, 24 months). In one embodiment, hydrated allograft bone was stored in the antimicrobial solution. For example, the implantable device, e.g., allograft bone, can be stored in the storage solution for from about 2 hours to about 24 months, e.g., from about 2 weeks to about 6 weeks. In some embodiments, the step of keeping further comprises keeping the implantable device in the storage solution at 25° C. or at ambient temperature.

In another embodiment of this aspect, the method of the present disclosure is used in combination with an allograft method, xenograft method, alloplastic graft method, or orthopedic biocomposite method. In one embodiment, the biocomposite contains hydroxyapatite (HA) or octacalcium phosphate (OCP).

In yet another aspect, this disclosure further provides a kit for storing a hydrated implantable device, including: (i) a first sealable container; (ii) a second sealable container housed within the first sealable container; and (iii) a third container containing a storage solution containing a zinc compound, wherein the storage solution exhibits antimicrobial activity of inhibiting or controlling growth of microbial organisms and is capable of maintaining the implantable device in a hydrated state.

In one embodiment, the kit may also include informational material. The informational material can be descriptive, instructional, marketing or other material that relates to the methods described herein. The informational material of the kits is not limited in its form. In one embodiment, the informational material can include information about production of the system, such as concentration, date of expiration, batch or production site information, and so forth of the storage solution. The information can be provided in a variety of formats, including printed text, computer-readable material, video recording, or audio recording, or information that contains a link or address to substantive material.

The kit optionally includes a device suitable for measuring or loading the storage solution. The device can be provided pre-loaded with one or both of the agents or can be empty, but suitable for loading.

In another aspect, the present disclosure relates to a method of inhibiting the growth of bacterium in allograft tissue comprising mechanically applying an antimicrobial solution to the allograft. The present disclosure also relates to inhibiting or controlling growth of microbial organisms, comprising mechanically applying an antimicrobial solution to the microbial organism, wherein the antimicrobial solution exhibits antimicrobial activity.

The term "antimicrobial activity" means in the context of the present disclosure that the antimicrobial of the disclosure is active in inhibiting or controlling growth of microbial organisms, including fungal organisms and/or bacterial organisms, such as gram-positive and gram-negative bacteria. The antimicrobial activity can occur after the allograft is implanted into the body.

In some embodiments, the antibacterial activity is the activity for bacterium selected from the group consisting of Pseudomonas aeruginosa, Staphylococcus aureus, Aspergillus brasiliensis spores, and Escherichia coli.

The present disclosure also relates to an antimicrobial composition comprising an antimicrobial agent of the disclosure and pharmaceutically acceptable vehicles, excipients, diluents, and adjuvants.

Zinc compounds suitable for use in the antimicrobial solution of the present disclosure include inorganic zinc compounds, such as mineral acid zinc salts. Examples of inorganic zinc compounds include, but are not limited to, zinc chloride, zinc sulfate, zinc phosphate, zinc carbonate, and zinc nitrate, zinc chlorate, zinc chromate or combinations thereof.

Zinc compounds which can be used in the antimicrobial solution can also be zinc salts of organic acids. Examples of organic acid zinc salts include, but are not limited to, zinc acetate, zinc formate, zinc propionate, zinc gluconate, bis(maltolato)zinc, zinc acexamate, zinc aspartate, bis(maltolato)zinc(II) [Zn(ma)$_2$], bis(2-hydroxypyridine-N-oxido) zinc(II) [Zn(hpo)$_2$], bis(allixinato) Zn(II) [Zn(alx)$_2$], bis(6-methylpicolinato) Zn(II) [Zn(6mpa)$_2$], bis(aspirinato)zinc (II), bis(pyrrole-2-carboxylato)zinc [Zn(pc)$_2$], bis(alpha-furonic acidato)zinc [Zn(fa)$_2$], bis(thiophene-2-carboxylato) zinc [Zn(tc)$_2$], bis(thiophene-2-acetato)zinc [Zn(ta)$_2$], (N-acetyl-L-cysteinato) Zn(II) [Zn(nac)], zinc(II)/poly(γ-glutamic acid) [Zn(γ-pga)], bis(pyrrolidine-N-dithiocarbamate)zinc(II) [Zn(pdc)$_2$], zinc(II) L-lactate [Zn(lac)$_2$], zinc(II) D-(2)-quinic acid [Zn(qui)$_2$], bis(1,6-dimethyl-3-hydroxy-5-methoxy-2-pentyl-1,4-dihydropyridine-4-thionato)zinc(II) [Zn(tanm)$_2$], β-alanyl-L-histidinato zinc(II) (AHZ), or the like, or combinations thereof. In another embodiment, the organic acid of zinc salt is a naturally occurring fatty acid.

In one embodiment, concentrations of zinc chloride of about 1 mM to about 10 mM can be used as the antimicrobial solution. In an alternative embodiment, zinc salts can be used in the antimicrobial solution in concentrations of about 30 mM to about 100 mM.

In one embodiment, allograft bone was soaked in the antimicrobial solution. For example, the allograft bone can be soaked in the antimicrobial solution for from about 2 hours to about 24 hours, e.g., from about 2 hours to about 6 hours. In some embodiments, the antimicrobial solution is applied by soaking the allograft tissue in the antimicrobial solution for about 2 hours to about 24 hours. In some embodiments, the antimicrobial solution comprises about 0.1% zinc chloride to about 0.5% zinc chloride, e.g., about 0.3% zinc chloride to about 0.5% zinc chloride.

Alternatively, allograft bone was rinsed with the antimicrobial solution such as by the Shake Flask Method (ASTM E2149). For example, the allograft bone can be rinsed in the antimicrobial solution for from about 45 minutes to about 120 minutes.

For purposes of the following description, allograft bone is referred to as an exemplary tissue that may be processed according to the present method. However, those skilled in the art will recognize that other tissues, including but not limited to autograft bone, xenograft bone, allograft cartilage, allograft amniotic tissue, other porous tissues, synthetic porous materials, and various soft tissues, may be processed according to the principles defined herein, without departing from the spirit of the disclosure exemplified herein by reference to allograft bone material. A suitable allograft cartilage is manufactured by Anthrex as BIOCARTILAGE. In one embodiment, the soft tissue is a ligament or a tendon.

In another embodiment of this aspect, the method of the present disclosure is used in combination with an allograft method, autograft method, xenograft method, alloplastic graft method, or orthopedic biocomposite method.

In another embodiment of this aspect, the patient is a mammalian animal. In another embodiment of this aspect, the patient is a human.

The disclosure can be further illustrated by the following examples thereof, although it will be understood that these examples are included merely for purposes of illustration and are not intended to limit the scope of the disclosure unless otherwise specifically indicated. All percentages, ratios, and parts herein, in the Specification, Examples, and Claims, are by weight and are approximations unless otherwise stated.

Definitions

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

The terms "increased," "increase" or "enhance" or "activate" are all used herein to generally mean an increase by a statically significant amount; for the avoidance of any doubt, the terms "increased," "increase" or "enhance" or "activate" means an increase of at least 10% as compared to a reference level, for example, an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

"Sample," "test sample," and "patient sample" may be used interchangeably herein. The sample can be a sample of serum, urine plasma, amniotic fluid, cerebrospinal fluid, cells, or tissue. Such a sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as antibodies. The sample may be any tissue sample from the subject. The sample may comprise protein from the subject.

The term "disease" as used herein is intended to be generally synonymous and is used interchangeably with the terms "disorder" and "condition" (as in medical condition), in that all reflect an abnormal condition of the human or animal body or of one of its parts that impairs normal functioning, is typically manifested by distinguishing signs and symptoms and causes the human or animal to have a reduced duration or quality of life.

Throughout this disclosure, percent (%) values of a solution of zinc compound, such as zinc chloride, refers to "wt %."

As used herein, the term "in vitro" refers to events that occur in an artificial environment, e.g., in a test tube or reaction vessel, cell culture, etc., rather than within a multicellular organism.

As used herein, the term "in vivo" refers to events that occur within a multi-cellular organism, such as a non-human animal.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition that is "substantially free" from Y may be completely free from Y. Where necessary, the word "substantially" may be omitted from the definition of the disclosure.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither, or both limits are included in the smaller ranges is also encompassed within the disclosure, subject to any specifically excluded limit in the stated range. Where the stated range includes one or both of the limits, ranges excluding either or both of those included limits are also included in the disclosure.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the disclosure unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise. In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present disclosure. Nothing herein is to be construed as an admission that the present disclosure is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1

Materials and Methods

A suspension of test organism Staphylococcus aureus (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test substance of zinc chloride at specified concentrations of 0.1%, 0.3%, and 0.5% from a 1% stock solution at specified exposure times of 10 minutes, 2 hours, 6 hours, and 24 hours at a temperature of 37±1° C. (37.2° C.). Latheen broth and 1% sodium bicarbonate (9.9 mL) were used as a neutralizer. After exposure, an aliquot of the suspension was transferred to the neutralizer and was assayed for survivors. Tables 1-3 show the results of controls used in this example.

TABLE 1

CONTROL RESULTS

| | Type of Control | Results |
|---|---|---|
| Purity | Staphylococcus aureus (ATCC 6538) | Pure |
| | Neutralizer Sterility Control | No Growth |

TABLE 2

TEST POPULATION CONTROL RESULTS

| | | Results | | | |
|---|---|---|---|---|---|
| Test Organism | Timepoint | CFU/mL | $Log_{10}$ | Average $Log_{10}$ | Geometric Mean |
| Staphylococcus aureus (ATCC 6538) | $T_0$ 24 Hour | $3.5 \times 10^6$ $6.2 \times 10^4$ | 6.54 4.79 | 5.67 | $4.68 \times 10^5$ |

CFU = Colony Forming Units

TABLE 3

NEUTRALIZATION CONFIRMATION CONTROL RESULTS

| | | Neutralization Confirmation (CFU) | | |
|---|---|---|---|---|
| Test Substance | Test Organism | Numbers Control | Test Substance Results | Pass/Fail ($Log_{10}$ Difference) |
| Zinc chloride Lot# A0340879 | Staphylococcus aureus (ATCC 6538) | 34, 19 | 15, 13 | Pass (0.28) |

CFU = Colony Forming Units

Results

Table 4 shows test results to evaluate antimicrobial effectiveness on Staphylococcus aureus for the experiments of this example. Table 5 shows calculated data for percent and Log 10 reduction of the test results shown in Table 4.

TABLE 4

TEST RESULTS FOR Staphylococcus aureus

| DILUTION | Exposure Time | | | |
|---|---|---|---|---|
| (VOLUME PLATED) | 10 minutes | 2 hours | 6 hours | 24 hours |
| | | Number of Survivors | | |
| Test Substance: 0.1% Zinc Chloride | | | | |
| $10^0$ (1.00 mL) | T, T | 56, 42 | 22, 23 | 4, 3 |
| $10^0$ (0.100 mL) | T, T | 3, 3 | 3, 4 | 0, 0 |
| $10^1$ (0.100 mL) | T, T | 1, 0 | 2, 0 | 0, 0 |
| $10^2$ (0.100 mL) | 66, 69 | 0, 0 | 0, 0 | 0, 0 |
| $10^3$ (0.100 mL) | 9, 19 | 0, 0 | 0, 1 | 0, 0 |
| Test Substance: 0.3% Zinc Chloride | | | | |
| $10^0$ (1.00 mL) | T, T | 0, 2 | 0, 0 | 0, 0 |
| $10^0$ (0.100 mL) | T, T | 0, 0 | 0, 0 | 0, 0 |
| $10^1$ (0.100 mL) | 60, 57 | 0, 0 | 0, 0 | 0, 0 |
| $10^2$ (0.100 mL) | 5, 6 | 0, 0 | 0, 0 | 0, 0 |
| $10^3$ (0.100 mL) | 1, 3 | 0, 0 | 0, 0 | 0, 0 |
| Test Substance: 0.5% Zinc Chloride | | | | |
| $10^0$ (1.00 mL) | T, T | 2, 0 | 0, 0 | 0, 0 |
| $10^0$ (0.100 mL) | T, T | 0, 0 | 0, 0 | 0, 0 |
| $10^1$ (0.100 mL) | 32, 26 | 0, 0 | 0, 0 | 0, 0 |
| $10^2$ (0.100 mL) | 5, 5 | 0, 0 | 0, 0 | 0, 0 |
| $10^3$ (0.100 mL) | 0, 1 | 0, 0 | 0, 0 | 0, 0 |

T = Too Numerous To Count (>300 colonies)
A value of <1 was used in place of zero for calculation purposes.

TABLE 5

CALCULATED DATA FOR Staphylococcus aureus

| Test Substance | Exposure Time | CFU/mL in Test Population Control ($Log_{10}$) | CFU/mL of Survivors | $Log_{10}$ Survivors | Percent Reduction | $Log_{10}$ Reduction |
|---|---|---|---|---|---|---|
| 0.1% Zinc Chloride | 10 minutes | $4.68 \times 10^5$ (5.67) | $6.8 \times 10^5$ | 5.83 | None | None |
| | 2 hours | | $4.9 \times 10^2$ | 2.69 | >99.8% | 2.98 |
| | 6 hours | | $2.3 \times 10^2$ | 2.36 | >99.9% | 3.31 |
| | 24 hours | | $4 \times 10^1$ | 1.60 | 99.99% | 4.07 |
| 0.3% Zinc Chloride | 10 minutes | | $5.9 \times 10^4$ | 4.77 | 87.4% | 0.90 |
| | 2 hours | | $1 \times 10^1$ | 1.00 | >99.99% | 4.67 |
| | 6 hours | | <5 | <0.70 | >99.99% | >4.97 |
| | 24 hours | | <5 | <0.70 | >99.99% | >4.97 |

TABLE 5-continued

CALCULATED DATA FOR *Staphylococcus aureus*

| Test Substance | Exposure Time | CFU/mL in Test Population Control (Log$_{10}$) | CFU/mL of Survivors | Log$_{10}$ Survivors | Percent Reduction | Log$_{10}$ Reduction |
|---|---|---|---|---|---|---|
| 0.5% Zinc Chloride | 10 minutes | | 2.9 × 10$^4$ | 4.46 | 93.8% | 1.21 |
| | 2 hours | | 1 × 10$^1$ | 1.00 | >99.99% | 4.67 |
| | 6 hours | | <5 | <0.70 | >99.99% | >4.97 |
| | 24 hours | | <5 | <0.70 | >99.99% | >4.97 |

CFU = Colony Forming Units

The geometric mean and average log$_{10}$ values were used for the population control.

Example 2

Materials and Methods

A suspension of test organism Staphylococcus aureus (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test substance of zinc chloride (4.75 mL) with allograft bone 0.25 g at specified concentrations of 0.3% and 0.5% from a 1% stock solution at specified exposure times of 2 hours, 6 hours, and 24 hours at a temperature of 37±1° C. Latheen broth and 1% sodium bicarbonate (9.9 mL) were used as a neutralizer. After exposure, an aliquot of the suspension was transferred to the neutralizer and was assayed for survivors. Tables 6-8 show the results of controls used in this example.

TABLE 6

CONTROL RESULTS

| Type of Control | | Results |
|---|---|---|
| Purity | *Staphylococcus aureus* (ATCC 6538) | Pure |
| | Neutralizer Sterility Control | No Growth |

TABLE 7

TEST POPULATION CONTROL RESULTS

| | | Results | | | |
|---|---|---|---|---|---|
| Test Organism | Timepoint | CFU/mL | Log$_{10}$ | Average Log$_{10}$ | Geometric Mean |
| *Staphylococcus aureus* (ATCC 6538) | T$_0$ | 1.15 × 10$^6$ | 6.06 | 5.83 | 6.76 × 10$^5$ |
| | 24 Hour | 3.9 × 10$^5$ | 5.59 | | |

CFU = Colony Forming Units

TABLE 8

NEUTRALIZATION CONFIRMATION CONTROL RESULTS

| | | Neutralization Confirmation (CFU) | | |
|---|---|---|---|---|
| Test Substance | Test Organism | Numbers Control | Test Substance Results | Pass/Fail (Log$_{10}$ Difference) |
| Zinc chloride | *Staphylococcus aureus* (ATCC 6538) | 33, 34 | 30, 21 | Pass (0.12) |

CFU = Colony Forming Units

Results

Table 9 shows test results for Staphylococcus aureus for the experiments of this example. Table 10 shows calculated data of percent and Log 10 reduction for the test results shown in Table 9.

TABLE 9

TEST RESULTS FOR *Staphylococcus aureus*

| DILUTION (VOLUME PLATED) | Number of Survivors Exposure Time | | | | | | | | |
|---|---|---|---|---|---|---|---|---|---|
| | 2 hours | | | 6 hours | | | 24 hours | | |
| | Rep 1 | Rep 2 | Rep 3 | Rep 1 | Rep 2 | Rep 3 | Rep 1 | Rep 2 | Rep 3 |
| Test Substance: 0.3% Zinc Chloride with allograft bone | | | | | | | | | |
| 10$^0$ (1.00 mL) | T, T | T, T | T, T | T, T | T, T | T, T | 12, 2 | 23, 25 | 8, 7 |
| 10$^0$ (0.100 mL) | T, T | T, T | T, T | T, T | T, T | T, T | 0, 4 | 1, 8 | 0, 0 |
| 10$^1$ (0.100 mL) | T, T | T, T | T, T | 117, 151 | 210, 224 | 254, 206 | 0, 0 | 1, 1 | 0, 0 |
| 10$^2$ (0.100 mL) | 69, 63 | 54, 71 | 85, 101 | 14, 3 | 33, 30 | 25, 32 | 0, 0 | 0, 0 | 0, 0 |
| 10$^3$ (0.100 mL) | 8, 9 | 7, 9 | 13, 12 | 1, 1 | 3, 3 | 3, 5 | 0, 0 | 0, 0 | 0, 0 |
| Test Substance: 0.5% Zinc Chloride with allograft bone | | | | | | | | | |
| 10$^0$ (1.00 mL) | T, T | T, T | T, T | T, T | T, T | T, T | 9, 15 | 5, 5 | 5, 3 |
| 10$^0$ (0.100 mL) | T, T | T, T | T, T | T, T | T, T | T, T | 3, 2 | 0, 1 | 1, 0 |

TABLE 9-continued

TEST RESULTS FOR Staphylococcus aureus

| DILUTION | Number of Survivors Exposure Time | | | | | | | | |
|---|---|---|---|---|---|---|---|---|---|
| (VOLUME | 2 hours | | | 6 hours | | | 24 hours | | |
| PLATED) | Rep 1 | Rep 2 | Rep 3 | Rep 1 | Rep 2 | Rep 3 | Rep 1 | Rep 2 | Rep 3 |
| $10^1$ (0.100 mL) | T, T | T, T | T, T | 78, 73 | 67, 66 | 68, 59 | 0, 0 | 0, 0 | 0, 0 |
| $10^2$ (0.100 mL) | 74, 70 | 130, 117 | 86, 74 | 6, 4 | 4, 8 | 2, 2 | 0, 0 | 0, 0 | 0, 0 |
| $10^3$ (0.100 mL) | 15, 9 | 11, 17 | 13, 9 | 1, 0 | 0, 0 | 1, 0 | 0, 0 | 0, 0 | 0, 0 |

Rep = Replicate
T = Too Numerous To Count (>300 colonies)

TABLE 10

CALCULATED DATA FOR Staphylococcus aureus

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.3% Zinc Chloride with allograft bone | 2 hours | $6.76 \times 10^5$ (5.83) | $6.6 \times 10^5$ $6.3 \times 10^5$ $9.3 \times 10^6$ | 5.82 5.80 5.97 | $7.24 \times 10^5$ (5.86) | No Reduction |
| | 6 hours | | $1.34 \times 10^5$ $2.17 \times 10^5$ $2.30 \times 10^5$ | 5.13 5.34 5.36 | $1.91 \times 10^5$ (5.28) | 71.7% (0.55) |
| | 24 hours | | $1.2 \times 10^2$ $2.4 \times 10^2$ $8 \times 10^1$ | 2.08 2.38 1.90 | $1.32 \times 10^2$ (2.12) | >99.9% (3.71) |
| 0.5% Zinc Chloride with allograft bone | 2 hours | | $7.2 \times 10^5$ $1.24 \times 10^6$ $8.0 \times 10^5$ | 5.86 6.09 5.90 | $8.91 \times 10^5$ (5.95) | No Reduction |
| | 6 hours | | $7.6 \times 10^5$ $6.7 \times 10^4$ $6.4 \times 10^4$ | 4.88 4.83 4.81 | $6.92 \times 10^4$ (4.84) | 89.8% (0.99) |
| | 24 hours | | $1.2 \times 10^2$ $5 \times 10^1$ $4 \times 10^1$ | 2.08 1.70 1.60 | $6.17 \times 10^1$ (1.79) | 99.99% (4.04) |

CFU = Colony Forming Units

The geometric mean and average $log_{10}$ values were used for the test replicates and population control.

Example 3

Materials and Methods

A suspension of test organism Staphylococcus aureus (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test BIOCARTILAGE from Anthrex substance of 4.75 mL of zinc chloride at specified concentrations of 0.3% and 0.5% containing 0.25 g BioCartilage® at specified exposure times of 6 hours and 24 hours at a temperature of 37±1° C. Latheen broth and 1% sodium bicarbonate (9.9 mL) were used as a neutralizer. After exposure, an aliquot of the suspension was transferred to the neutralizer and was assayed for survivors. The suspension was also exposed to a test Amnion Matrix from Anthrex substance of 9.5 mL of zinc chloride at specified concentrations of 0.3% and 0.5% containing Amnion Matrix (1 count) at specified exposure times of 6 hours and 24 hours at a temperature of 37±1° C. Latheen broth and 1% sodium bicarbonate (9.9 mL) were used as a neutralizer. After exposure, an aliquot of the suspension was transferred to the neutralizer and was assayed for survivors. Tables 11-13 show controls used in this example.

TABLE 11

CONTROL RESULTS

| Type of Control | | Results |
|---|---|---|
| Purity | Staphylococcus aureus (ATCC 6538) | Pure |
| Neutralizer Sterility Control | | No Growth |

TABLE 12

TEST POPULATION CONTROL RESULTS

| | | Results | |
|---|---|---|---|
| Test Organism | Time Point | CFU/mL | $Log_{10}$ |
| Staphylococcus aureus (ATCC 6538) | Time Zero | $1.54 \times 10^6$ | 6.19 |
| | 24 Hours | $9.8 \times 10^4$ | 4.99 |
| | | Average $Log_{10}$: 5.59 | |
| | | Geometric Mean: $3.89 \times 10^5$ | |

CFU = Colony Forming Units

TABLE 13

NEUTRALIZATION CONFIRMATION CONTROL RESULTS

| Test Substance | Test Organism | Numbers Control | Neutralization Confirmation (CFU) Test Substance Results | Pass/Fail ($Log_{10}$ Difference) |
|---|---|---|---|---|
| Zinc chloride (with BIOCARTILAGE) | Staphylococcus aureus (ATCC 6538) | 36, 29 | 38, 36 | Pass (−0.05) |
| Zinc chloride (with Amnion Matrix) | | 36, 29 | 59, 46 | Pass (−0.20) |

CFU = Colony Forming Units

Table 14 shows test results for Staphylococcus aureus for the BIOCARTILAGE experiments of this example. Table 15 shows test results for Staphylococcus aureus for the Amnion Matrix experiments of this example. Table 16 shows calculated data of percent and Log 10 reduction for the test results shown in Table 14. Table 17 shows calculated data of percent and Log 10 reduction for the test results shown in Table 15.

TABLE 14

SHOWS TEST RESULTS FOR ZINC CHLORIDE (with BIOCARTILAGE)

| DILUTION (VOLUME PLATED) | Test Organism: *Staphylococcus aureus* (ATCC 6538) Number of Survivors Exposure Time | | | |
|---|---|---|---|---|
| | 6 hours | | 24 hours | |
| | Replicate 1 | Replicate 2 | Replicate 1 | Replicate 2 |
| Test Substance: 0.3% Zinc chloride with BIOCARTILAGE | | | | |
| $10^0$ (1.00 mL) | 35, 42 | 51, 28 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |
| Test Substance: 0.5% Zinc chloride with BIOCARTILAGE | | | | |
| $10^0$ (1.00 mL) | 29, 21 | 35, 41 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |

TABLE 15

SHOWS TEST RESULTS FOR ZINC CHLORIDE (with Amnion Matrix)

| DILUTION (VOLUME PLATED) | Test Organism: *Staphylococcus aureus* (ATCC 6538) Number of Survivors Exposure Time | | | |
|---|---|---|---|---|
| | 6 hours | | 24 hours | |
| | Replicate 1 | Replicate 2 | Replicate 1 | Replicate 2 |
| Test Substance: 0.3% Zinc chloride with Amnion Matrix | | | | |
| $10^0$ (1.00 mL) | 8, 7 | 19, 18 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |
| Test Substance: 0.5% Zinc chloride with Amnion Matrix | | | | |
| $10^0$ (1.00 mL) | 84, 74 | 4, 2 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |

TABLE 16

CALCULATED DATA FOR ZINC CHLORIDE (with BIOCARTILAGE)

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.3% Zinc chloride with BIO-CARTI-LAGE | 6 hours | $3.89 \times 10^5$ (5.59) | $3.9 \times 10^2$ $4.0 \times 10^2$ | 2.59 2.60 | $3.98 \times 10^2$ (2.60) | >99.8% (2.99) |
| | 24 hours | | <5 <5 | <0.70 <0.70 | <5.01 (<0.70) | >99.99% (>4.89) |
| 0.5% Zinc chloride with BIO-CARTI-LAGE | 6 hours | | $2.5 \times 10^2$ $3.8 \times 10^2$ | 2.40 2.58 | $3.09 \times 10^2$ (2.49) | 99.9% (3.10) |
| | 24 hours | | <5 <5 | <0.70 <0.70 | <5.01 (<0.70) | >99.99% (>4.89) |

CFU = Colony Forming Units
A value of <1 was used in place of zero for calculation purposes.
The geometric mean and average $log_{10}$ values were used for the population control.
The geometric mean and average $log_{10}$ values were used for the test replicates to determine reductions.

TABLE 17

CALCULATED DATA FOR ZINC CHLORIDE (with Amnion Matrix)

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.3% Zinc chloride with Amnion Matrix | 6 hours | $3.89 \times 10^5$ (5.59) | $8 \times 10^1$ $1.9 \times 10^2$ | 1.90 2.28 | $1.23 \times 10^2$ (2.09) | >99.9% (3.50) |
| | 24 hours | | <5 <5 | <0.70 <0.70 | <5.01 (<0.70) | >99.99% (>4.89) |
| 0.5% Zinc chloride with Amnion Matrix | 6 hours | | $7.9 \times 10^2$ $3 \times 10^1$ | 2.90 1.48 | $1.55 \times 10^2$ (2.19) | >99.9% (3.40) |
| | 24 hours | | <5 <5 | <0.70 <0.70 | <5.01 (<0.70) | >99.99% (>4.89) |

CFU = Colony Forming Units
A value of <1 was used in place of zero for calculation purposes.
The geometric mean and average $log_{10}$ values were used for the population control.
The geometric mean and average $log_{10}$ values were used for the test replicates to determine reductions.

Example 4

A suspension of test organism Staphylococcus aureus (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test substance of zinc chloride at specified concentrations of 0.1%, 0.3%, and 0.5% from a 1% stock solution at specified exposure times of 10 minutes, 2 hours, 6 hours, and 24 hours at a temperature of 37±1° C. (37.2° C.). Latheen broth and 1% sodium bicarbonate (9.9 mL) were used as a neutralizer. After exposure, an aliquot of the suspension was transferred to the neutralizer and was assayed for survivors. Tables 18-21 show the results of the controls used in this example.

TABLE 18

CONTROL RESULTS

| Type of Control | | Results |
|---|---|---|
| Purity | *Staphylococcus aureus* (ATCC 6538) | Pure |
| | Neutralizer Sterility Control | No Growth |

TABLE 19

TEST POPULATION CONTROL RESULTS

| | | Results | | | |
|---|---|---|---|---|---|
| Test Organism | Time-point | CFU/mL | $\text{Log}_{10}$ | Average $\text{Log}_{10}$ | Geometric Mean |
| *Staphylococcus aureus* (ATCC 6538) | $T_0$ | $3.5 \times 10^6$ | 6.54 | 5.67 | $4.68 \times 10^5$ |
| | 24 Hour | $6.2 \times 10^4$ | 4.79 | | |

CFU = Colony Forming Units

TABLE 20

NEUTRALIZATION CONFIRMATION CONTROL RESULTS

| | | Neutralization Confirmation (CFU) | | |
|---|---|---|---|---|
| Test Substance | Test Organism | Numbers Control | Test Substance Results | Pass/Fail ($\text{Log}_{10}$ Difference) |
| Zinc chloride Lot# A0340879 | *Staphylococcus aureus* (ATCC 6538) | 34, 19 | 15, 13 | Pass (0.28) |

CFU = Colony Forming Units

Table 21 shows test results to evaluate antimicrobial effectiveness on Staphylococcus aureus for the experiments of this example. Table 22 shows calculated data for percent and Log 10 reduction of the test results shown in Table 21.

TABLE 21

TEST RESULTS FOR *Staphylococcus aureus*

| DILUTION (VOLUME PLATED) | Exposure Time | | | |
|---|---|---|---|---|
| | 10 minutes | 2 hours | 6 hours | 24 hours |
| | Number of Survivors | | | |
| Test Substance: 0.1% Zinc Chloride | | | | |
| $10^0$ (1.00 mL) | T, T | 56, 42 | 22, 23 | 4, 3 |
| $10^0$ (0.100 mL) | T, T | 3, 3 | 3, 4 | 0, 0 |
| $10^1$ (0.100 mL) | T, T | 1, 0 | 2, 0 | 0, 0 |
| $10^2$ (0.100 mL) | 66, 69 | 0, 0 | 0, 0 | 0, 0 |
| $10^3$ (0.100 mL) | 9, 19 | 0, 0 | 0, 1 | 0, 0 |
| Test Substance: 0.3% Zinc Chloride | | | | |
| $10^0$ (1.00 mL) | T, T | 0, 2 | 0, 0 | 0, 0 |
| $10^0$ (0.100 mL) | T, T | 0, 0 | 0, 0 | 0, 0 |
| $10^1$ (0.100 mL) | 60, 57 | 0, 0 | 0, 0 | 0, 0 |
| $10^2$ (0.100 mL) | 5, 6 | 0, 0 | 0, 0 | 0, 0 |
| $10^3$ (0.100 mL) | 1, 3 | 0, 0 | 0, 0 | 0, 0 |
| Test Substance: 0.5% Zinc Chloride | | | | |
| $10^0$ (1.00 mL) | T, T | 2, 0 | 0, 0 | 0, 0 |
| $10^0$ (0.100 mL) | T, T | 0, 0 | 0, 0 | 0, 0 |
| $10^1$ (0.100 mL) | 32, 26 | 0, 0 | 0, 0 | 0, 0 |
| $10^2$ (0.100 mL) | 5, 5 | 0, 0 | 0, 0 | 0, 0 |
| $10^3$ (0.100 mL) | 0, 1 | 0, 0 | 0, 0 | 0, 0 |

T = Too Numerous To Count (>300 colonies)
A value of <1 was used in place of zero for calculation purposes.

TABLE 22

CALCULATED DATA FOR *Staphylococcus aureus*

| Test Substance | Exposure Time | CFU/mL in Test Population Control ($\text{Log}_{10}$) | CFU/mL of Survivors | $\text{Log}_{10}$ Survivors | Percent Reduction | $\text{Log}_{10}$ Reduction |
|---|---|---|---|---|---|---|
| 0.1% Zinc Chloride | 10 minutes | $4.68 \times 10^5$ (5.67) | $6.8 \times 10^5$ | 5.83 | None | None |
| | 2 hours | | $4.9 \times 10^2$ | 2.69 | >99.8% | 2.98 |
| | 6 hours | | $2.3 \times 10^2$ | 2.36 | >99.9% | 3.31 |
| | 24 hours | | $4 \times 10^1$ | 1.60 | 99.99% | 4.07 |
| 0.3% Zinc Chloride | 10 minutes | | $5.9 \times 10^4$ | 4.77 | 87.4% | 0.90 |
| | 2 hours | | $1 \times 10^1$ | 1.00 | >99.99% | 4.67 |
| | 6 hours | | <5 | <0.70 | >99.99% | >4.97 |
| | 24 hours | | <5 | <0.70 | >99.99% | >4.97 |
| 0.5% Zinc Chloride | 10 minutes | | $2.9 \times 10^4$ | 4.46 | 93.8% | 1.21 |
| | 2 hours | | $1 \times 10^1$ | 1.00 | >99.99% | 4.67 |
| | 6 hours | | <5 | <0.70 | >99.99% | >4.97 |
| | 24 hours | | <5 | <0.70 | >99.99% | >4.97 |

CFU = Colony Forming Units
The geometric mean and average $\log_{10}$ values were used for population control.

Example 5

A suspension of test organism Staphylococcus aureus (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test substance of zinc chloride (4.75 mL) with allograft bone 0.25 g at specified concentrations of 0.3% and 0.5% from a 1% stock solution at specified exposure times of 2 hours, 6 hours, and 24 hours at a temperature of 37±1° C. Latheen broth and 1% sodium bicarbonate (9.9 mL) were used as a neutralizer. After exposure, an aliquot of the suspension was transferred to the neutralizer and was assayed for survivors. Tables 23-24 show the results of the controls used in this example.

TABLE 23

CONTROL RESULTS

| Type of Control | | Results |
|---|---|---|
| Purity | *Staphylococcus aureus* (ATCC 6538) | Pure |
| | Neutralizer Sterility Control | No Growth |

TABLE 24

TEST POPULATION CONTROL RESULTS

| | | | | Results | |
|---|---|---|---|---|---|
| Test Organism | Timepoint | CFU/mL | $Log_{10}$ | Average $Log_{10}$ | Geometric Mean |
| Staphylococcus aureus (ATCC 6538) | $T_0$ 24 Hour | $1.15 \times 10^6$ $3.9 \times 10^5$ | 6.06 5.59 | 5.83 | $6.76 \times 10^5$ |

CFU = Colony Forming Units

TABLE 25

NEUTRALIZATION CONFIRMATION CONTROL RESULTS

| | | Neutralization Confirmation (CFU) | | |
|---|---|---|---|---|
| Test Substance | Test Organism | Numbers Control | Test Substance Results | Pass/Fail ($Log_{10}$ Difference) |
| Zinc chloride | Staphylococcus aureus (ATCC 6538) | 33, 34 | 30, 21 | Pass (0.12) |

CFU = Colony Forming Units

Table 26 shows the test results for Staphylococcus aureus for the experiments of this example. Table 27 shows the calculated data of percent and Log 10 reduction for the test results shown in Table 26.

TABLE 26

TEST RESULTS FOR Staphylococcus aureus

| DILUTION (VOLUME PLATED) | Number of Survivors Exposure Time | | | | | | | | |
|---|---|---|---|---|---|---|---|---|---|
| | 2 hours | | | 6 hours | | | 24 hours | | |
| | Rep 1 | Rep 2 | Rep 3 | Rep 1 | Rep 2 | Rep 3 | Rep 1 | Rep 2 | Rep 3 |
| Test Substance: 0.3% Zinc Chloride with allograft bone | | | | | | | | | |
| $10^0$ (1.00 mL) | T, T | T, T | T, T | T, T | T, T | T, T | 12, 2 | 23, 25 | 8, 7 |
| $10^0$ (0.100 mL) | T, T | T, T | T, T | T, T | T, T | T, T | 0, 4 | 1, 8 | 0, 0 |
| $10^1$ (0.100 mL) | T, T | T, T | T, T | 117, 151 | 210, 224 | 254, 206 | 0, 0 | 1, 1 | 0, 0 |
| $10^2$ (0.100 mL) | 69, 63 | 54, 71 | 85, 101 | 14, 3 | 33, 30 | 25, 32 | 0, 0 | 0, 0 | 0, 0 |
| $10^3$ (0.100 mL) | 8, 9 | 7, 9 | 13, 12 | 1, 1 | 3, 3 | 3, 5 | 0, 0 | 0, 0 | 0, 0 |
| Test Substance: 0.5% Zinc Chloride with allograft bone | | | | | | | | | |
| $10^0$ (1.00 mL) | T, T | T, T | T, T | T, T | T, T | T, T | 9, 15 | 5, 5 | 5, 3 |
| $10^0$ (0.100 mL) | T, T | T, T | T, T | T, T | T, T | T, T | 3, 2 | 0, 1 | 1, 0 |
| $10^1$ (0.100 mL) | T, T | T, T | T, T | 78, 73 | 67, 66 | 68, 59 | 0, 0 | 0, 0 | 0, 0 |
| $10^2$ (0.100 mL) | 74, 70 | 130, 117 | 86, 74 | 6, 4 | 4, 8 | 2, 2 | 0, 0 | 0, 0 | 0, 0 |
| $10^3$ (0.100 mL) | 15, 9 | 11, 17 | 13, 9 | 1, 0 | 0, 0 | 1, 0 | 0, 0 | 0, 0 | 0, 0 |

Rep = Replicate
T = Too Numerous To Count (>300 colonies)

TABLE 27

CALCULATED DATA FOR Staphylococcus aureus

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.3% Zinc Chloride with allograft bone | 2 hours | $6.76 \times 10^5$ (5.83) | $6.6 \times 10^5$ $6.3 \times 10^5$ | 5.82 5.80 | $7.24 \times 10^5$ (5.86) | No Reduction |
| | 6 hours | | $9.3 \times 10^6$ $1.34 \times 10^5$ $2.17 \times 10^5$ $2.30 \times 10^5$ | 5.97 5.13 5.34 5.36 | $1.91 \times 10^5$ (5.28) | 71.7% (0.55) |
| | 24 hours | | $1.2 \times 10^2$ $2.4 \times 10^2$ $8 \times 10^1$ | 2.08 2.38 1.90 | $1.32 \times 10^2$ (2.12) | >99.9% (3.71) |
| 0.5% Zinc Chloride with allograft bone | 2 hours | | $7.2 \times 10^5$ $1.24 \times 10^6$ $8.0 \times 10^5$ | 5.86 6.09 5.90 | $8.91 \times 10^5$ (5.95) | No Reduction |
| | 6 hours | | $7.6 \times 10^5$ $6.7 \times 10^4$ $6.4 \times 10^4$ | 4.88 4.83 4.81 | $6.92 \times 10^4$ (4.84) | 89.8% (0.99) |
| | 24 hours | | $1.2 \times 10^2$ $5 \times 10^1$ $4 \times 10^1$ | 2.08 1.70 1.60 | $6.17 \times 10^1$ (1.79) | 99.99% (4.04) |

CFU = Colony Forming Units

The geometric mean and average Log 10 values were used for the test replicates and population control.

Example 6

A suspension of test organism Staphylococcus aureus (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test BioCartilage from Anthrex substance of 4.75 mL of zinc chloride at specified concentrations of 0.3% and 0.5% containing 0.25 g BioCartilage at specified exposure times of 6 hours and 24 hours at a temperature of 37±1° C. Latheen broth and 1% sodium bicarbonate (9.9 mL) were used as a neutralizer. After exposure, an aliquot of the suspension was transferred to the neutralizer and was assayed for survivors. The suspension was also exposed to a test Amnion Matrix from Anthrex substance of 9.5 mL of zinc chloride at specified concentrations of 0.3% and 0.5% containing Amnion Matrix (1 count) at specified exposure times of 6 hours and 24 hours at a temperature of 37±1° C. Latheen broth and 1% sodium bicarbonate (9.9 mL) were used as a neutralizer. After exposure, an aliquot of the suspension was transferred to the neutralizer and was assayed for survivors.

Tables 28-30 show controls used in this example.

TABLE 28

CONTROL RESULTS

| Type of Control | | Results |
| --- | --- | --- |
| Purity | *Staphylococcus aureus* (ATCC 6538) | Pure |
| Neutralizer Sterility Control | | No Growth |

TABLE 29

TEST POPULATION CONTROL RESULTS

| | | Results | |
| --- | --- | --- | --- |
| Test Organism | Time Point | CFU/mL | $Log_{10}$ |
| *Staphylococcus aureus* | Time Zero | $1.54 \times 10^6$ | 6.19 |
| (ATCC 6538) | 24 Hours | $9.8 \times 10^4$ | 4.99 |
| | Average $Log_{10}$: 5.59 Geometric Mean: $3.89 \times 10^5$ | | |

CFU = Colony Forming Units

TABLE 30

NEUTRALIZATION CONFIRMATION CONTROL RESULTS

| | | Neutralization Confirmation (CFU) | | |
| --- | --- | --- | --- | --- |
| Test Substance | Test Organism | Numbers Control | Test Substance Results | Pass/Fail ($Log_{10}$ Difference) |
| Zinc chloride (with BioCartilage) | *Staphylococcus aureus* (ATCC 6538) | 36, 29 | 38, 36 | Pass (−0.05) |
| Zinc chloride (with Amnion Matrix) | | 36, 29 | 59, 46 | Pass (−0.20) |

CFU = Colony Forming Units

Table 31 shows test results for Staphylococcus aureus for the BioCartilage experiments of this example. Table 32 shows test results for Staphylococcus aureus for the Amnion Matrix experiments of this example. Table 16 shows the calculated data of percent and Log 10 reduction for the test results shown in Table 31. Table 34 shows the calculated data of percent and Log 10 reduction for the test results shown in Table 32.

TABLE 31

SHOWS TEST RESULTS FOR ZINC CHLORIDE (with BioCartilage)

| DILUTION (VOLUME PLATED) | Test Organism: *Staphylococcus aureus* (ATCC 6538) Number of Survivors Exposure Time | | | |
| --- | --- | --- | --- | --- |
| | 6 hours | | 24 hours | |
| | Replicate 1 | Replicate 2 | Replicate 1 | Replicate 2 |
| Test Substance: 0.3% Zinc chloride with BioCartilage | | | | |
| $10^0$ (1.00 mL) | 35, 42 | 51, 28 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |
| Test Substance: 0.5% Zinc chloride with BioCartilage | | | | |
| $10^0$ (1.00 mL) | 29, 21 | 35, 41 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |

TABLE 32

SHOWS TEST RESULTS FOR ZINC CHLORIDE (with Amnion Matrix)

| DILUTION (VOLUME PLATED) | Test Organism: *Staphylococcus aureus* (ATCC 6538) Number of Survivors Exposure Time | | | |
| --- | --- | --- | --- | --- |
| | 6 hours | | 24 hours | |
| | Replicate 1 | Replicate 2 | Replicate 1 | Replicate 2 |
| Test Substance: 0.3% Zinc chloride with Amnion Matrix | | | | |
| $10^0$ (1.00 mL) | 8, 7 | 19, 18 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |
| Test Substance: 0.5% Zinc chloride with Amnion Matrix | | | | |
| $10^0$ (1.00 mL) | 84, 74 | 4, 2 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |

TABLE 33

CALCULATED DATA FOR ZINC CHLORIDE (with BioCartilage)

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
| --- | --- | --- | --- | --- | --- | --- |
| 0.3% Zinc chloride with BioCartilage | 6 hours | $3.89 \times 10^5$ (5.59) | $3.9 \times 10^2$ $4.0 \times 10^2$ | 2.59 2.60 | $3.98 \times 10^2$ (2.60) | >99.8% (2.99) |
| | 24 hours | | <5 <5 | <0.70 <0.70 | <5.01 (<0.70) | >99.99% (>4.89) |

TABLE 33-continued

CALCULATED DATA FOR
ZINC CHLORIDE (with BioCartilage)

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.5% Zinc chloride with BioCartilage | 6 hours 24 hours | | $2.5 \times 10^2$ $3.8 \times 10^2$ <5 <5 | 2.40 2.58 <0.70 <0.70 | $3.09 \times 10^2$ (2.49) <5.01 (<0.70) | 99.9% (3.10) >99.99% (>4.89) |

CFU = Colony Forming Units
A value of <1 was used in place of zero for calculation purposes. The geometric mean and average log10 values were used for population control. The geometric mean and average log10 values were used for the test replicates to determine reductions.

TABLE 34

CALCULATED DATA FOR ZINC
CHLORIDE (with Amnion Matrix)

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.3% Zinc chloride with Amnion Matrix | 6 hours 24 hours | $3.89 \times 10^5$ (5.59) | $8 \times 10^1$ $1.9 \times 10^2$ <5 <5 | 1.90 2.28 <0.70 <0.70 | $1.23 \times 10^2$ (2.09) <5.01 (<0.70) | >99.9% (3.50) >99.99% (>4.89) |
| 0.5% Zinc chloride with Amnion Matrix | 6 hours 24 hours | | $7.9 \times 10^2$ $3 \times 10^1$ <5 <5 | 2.90 1.48 <0.70 <0.70 | $1.55 \times 10^2$ (2.19) <5.01 (<0.70) | >99.9% (3.40) >99.99% (>4.89) |

CFU = Colony Forming Units
A value of <1 was used in place of zero for calculation purposes. The geometric mean and average $log_{10}$ values were used for population control. The geometric mean and average $log_{10}$ values were used for the test replicates to determine reductions.

It is to be understood that the above-described embodiments are illustrative of only a few of the many possible specific embodiments, which can represent applications of the principles of the disclosure. Numerous and varied other arrangements can be readily devised in accordance with these principles by those skilled in the art without departing from the spirit and scope of the disclosure.

What is claimed is:

1. A system for storing and preserving a hydrated implantable device, comprising:
   a first sealable container;
   a second sealable container housed within the first sealable container, wherein the second sealable container comprises an implantable device; and
   a storage solution comprising a zinc compound contained in the second sealable container, wherein the storage solution exhibits antimicrobial activity of inhibiting or controlling growth of microbial organisms and is capable of maintaining the implantable device in a hydrated state.

2. The system of claim 1, wherein the first sealable container or the second sealable container is a bag, a box, a jar or a tube.

3. The system of claim 1, wherein the second sealable container is sterilized.

4. The system of claim 1, wherein the second sealable container is removably housed within the first sealable container.

5. The system of claim 1, further comprising an insulation layer disposed between the first sealable container and the second sealable container, wherein the insulation layer separates a least a portion of the first sealable container from the second sealable container.

6. The system of claim 1, wherein the insulation layer is configured to reduce heat transmission between the first sealable container and the second sealable container.

7. The system of claim 1, wherein the first sealable container or the second sealable container is formed of steel, aluminum, glass, plastic, paper composite, or ceramic material.

8. The system of claim 7, wherein the plastic material comprises a polymer selected from the group consisting of polyolefins, polyesters, polyamide, polyvinylchloride, acrylic, polycarbonates, polyethylene naphthalate (PEN), polyethylene terephthalate (PET), polystyrene, polyurethane, and mixtures thereof.

9. The system of claim 1, wherein the zinc compound comprises an inorganic zinc compound.

10. The system of claim 9, wherein the inorganic zinc compound is selected from the group consisting of zinc chloride, zinc sulfate, zinc phosphate, zinc carbonate, and zinc nitrate, zinc chlorate, zinc chromate, and combinations thereof.

11. The system of claim 1, wherein the zinc compound comprises an organic zinc salt.

12. The system of claim 11, wherein the organic zinc salt is selected from the group consisting of zinc acetate, zinc formate, zinc propionate, zinc gluconate, bis(maltolato)zinc, zinc acexamate, zinc aspartate, bis(maltolato)zinc(II) [Zn(ma)$_2$], bis(2-hydroxypyridine-N-oxido)zinc(II) [Zn(hpo)$_2$], bis(allixinato) Zn(II) [Zn(alx)$_2$], bis(6-methylpicolinato) Zn(II) [Zn(6mpa)$_2$], bis(aspir-inato)zinc(II), bis(pyrrole-2-carboxylato)zinc [Zn(pc)$_2$], bis(alpha-furonic acidato)zinc [Zn(fa)$_2$], bis(thiophene-2-carboxylato)zinc [Zn(tc)$_2$], bis(thiophene-2-acetato)zinc [Zn(ta)$_2$], (N-acetyl-L-cysteinato) Zn(II) [Zn(nac)], zinc(II)/poly(γ-glutamic acid) [Zn(γ-pga)], bis(pyrrolidine-N-dithio-carbamate)zinc(II) [Zn(pdc)$_2$], zinc(II) L-lactate [Zn(lac)$_2$], zinc(II) D-(2)-quinic acid [Zn(qui)$_2$], bis(1,6-dimethyl-3-hydroxy-5-methoxy-2-pentyl-1, 4-dihydropyridine-4-thionato)zinc(II) [Zn(tanm)$_2$], β-alanyl-L-histidinato zinc(II) (AHZ), or the like, or combinations thereof.

13. The system of claim 1, wherein the storage solution comprises between about 1 mM and about 1 M zinc chloride.

14. The system of claim 1, wherein the storage solution comprises between about 0.1 wt % and about 20 wt % zinc chloride.

15. The system of claim 1, wherein the implantable device is tissue.

16. The system of claim 1, wherein the implantable device is a tissue graft.

17. The system of claim 16, wherein the tissue graft is selected from the group consisting of allograft bone, autograft bone, xenograft bone, allograft cartilage, amniotic tissue, ligament tissue, tendon tissue, porous tissue, and soft tissue.

18. The system of claim 16, wherein the implantable device is an allograft tissue.

19. The system of claim 17, wherein the soft tissue is a ligament or a tendon.

\* \* \* \* \*